United States Patent [19]

Whitehead et al.

[11] Patent Number: 4,578,069

[45] Date of Patent: Mar. 25, 1986

[54] BREATHABLE BAFFLE COMPOSITE

[75] Inventors: Howard A. Whitehead, Outagamie County, Wis.; Ralph V. Braun, Fulton County, Ga.

[73] Assignee: Kimberly-Clark Corporation, Neenah, Wis.

[21] Appl. No.: 639,467

[22] Filed: Aug. 10, 1984

[51] Int. Cl.[4] ............................................. A61F 13/16
[52] U.S. Cl. ........................................ 604/370; 604/372; 604/385 R; 604/389
[58] Field of Search ................ 604/370, 372, 385, 389

[56] References Cited

U.S. PATENT DOCUMENTS

| | | | |
|---|---|---|---|
| 3,595,235 | 7/1971 | Jespersen | 604/364 |
| 3,595,237 | 7/1971 | Sargent et al. | 604/370 |
| 3,952,347 | 4/1976 | Comerford et al. | 604/372 X |
| 3,989,867 | 11/1976 | Sisson | 604/370 X |
| 4,013,816 | 3/1977 | Sabee et al. | 604/372 X |
| 4,059,114 | 11/1977 | Richards | 604/370 X |
| 4,240,416 | 12/1980 | De Boich | 604/378 X |
| 4,315,507 | 2/1982 | Whitehead et al. | 604/370 X |
| 4,338,371 | 7/1982 | Correale et al. | 604/375 X |
| 4,341,216 | 7/1982 | Obenour | 604/370 |

*Primary Examiner*—Earl Nielsen

[57] ABSTRACT

A sanitary napkin having a gas permeable nonwoven baffle is provided in which a composite baffle is formed by joining webs of a meltblown polyolefin and a spunbonded polyolefin with the spunbonded polyolefin web providing a surface for garment attachment adhesive reception.

6 Claims, 2 Drawing Figures

BREATHABLE BAFFLE COMPOSITE

FIELD OF THE INVENTION

This invention relates to a sanitary napkin and particularly to a gas permeable baffle for sanitary napkins.

BACKGROUND OF THE INVENTION

Sanitary napkins are made of three separate components. An absorbent component is generally covered by a fluid permeable nonwoven cover material which is designed to abut the body of the wearer. A fluid impermeable baffle is provided to prevent leakage from the absorbent portion of the napkin into the garment of the wearer.

These baffles may be positioned directly against the absorbent with the cover in the form of a wrap which extends over and surrounds the baffle, or the baffle may be external to the wrap thereby providing an outer bottom-most surface for the sanitary napkin. Over the past decade, sanitary napkins having these external baffles have become more prevalent. One of the reasons for this is the increasing popularity of napkins of reduced bulk. These napkins which are of the panty liner or the maxi thin type do not require the cover to function as a complete pad wrap for purposes of stability. Also, ease of manufacture of these napkins dictates that the baffle be placed externally to the other components on the bottom of the napkin. Baffles have traditionally been made of a thermoplastic film which, while thin and inexpensive, tend to make noise when the wearer walks and also chafe the wearer's skin. In addition, while these baffles are fluid impermeable, they are also vapor impermeable. This means that perspiration resulting from wear is not easily removable from the napkin and vaporized moisture from napkin discharge remains within the napkin confines. Of course, this gas impermeable baffle prevents circulation of air which intensifies the odors associated with menstruation.

In addition, baffles which are external to the other napkin components, must have sufficient strength and integrity to receive garment attachment adhesive and resist tearing after the garment attachment adhesive is removed from the undergarment of the wearer when the napkin is changed.

Several attempts have been made in the past to design an acceptable fluid impermeable moisture permeable baffle. Representative prior art is U.S. Pat. No. 3,595,235 which discloses such a baffle without a description of how it is to be provided. U.S. Pat. No. 3,989,867 which discloses a baffle made of tapered hollow bosses in a polyethylene film which is allegedly impervious to fluids while pervious to gases. British Patent Application No. 2,035,092 discloses a backing for an absorbent article formed of a polyester-rayon nonwoven with coating of a liquid repellent breathable adhesive. U.S. Pat. No. 4,338,371 discloses a liquid impermeable gas permeable backing of spandex polyolefin fibers. U.S. Pat. No. 4,240,416 discloses a nonwoven cover of binder free synthetic fibers i.e., a spunbonded nonwoven web which has a wetting agent coated only on the body contact side. The patent discloses that the untreated back of this web is air permeable and fluid penetration resistant. U.S. Pat. No. 4,059,114 discloses a panty liner product with a meltblown baffle which is supposedly fluid impermeable and gas permeable made from a meltblown web of polypropylene fibers. There are several other patents, in addition, which treat coating of cellulosic material to withstand fluid penetration and depending on the nature of the treatment, these baffle layers may also be gas permeable.

Each of these patents provides baffles which are defective either from the standpoint of effective fluid blocking, strength which will resist tearing while providing a suitable adhesive anchor for garment attachment adhesive, or softness and quietness.

SUMMARY OF THE INVENTION

According to this invention, an external baffle for a sanitary napkin having a soft cloth-like feel is provided. This baffle has sufficient strength and internal integrity to provide an anchor for garment attachment adhesive while resisting tearing when the sanitary napkin is removed from the undergarment by the user. Gas permeability and protection against fluid leakage is provided by this baffle which is a composite of a meltblown web and a spunbonded web with the spunbonded web providing the exterior anchoring surface for garment attachment adhesive.

DETAILED DESCRIPTION OF THE INVENTION

Figure 1:
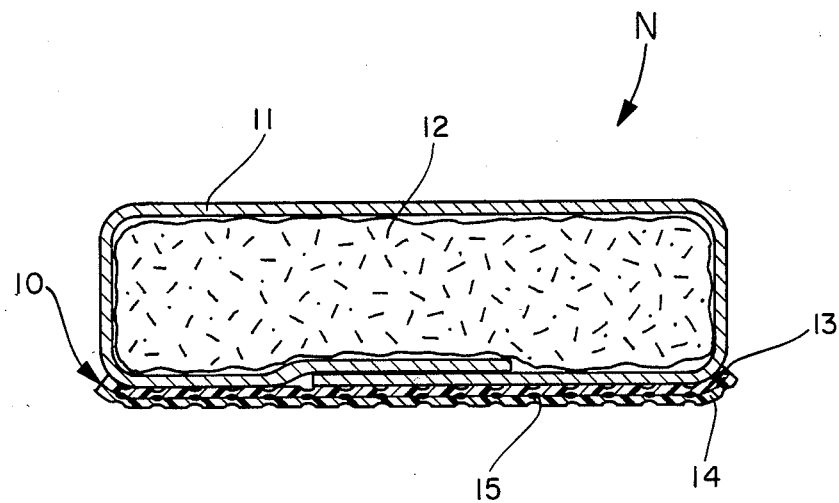
Figure 2:
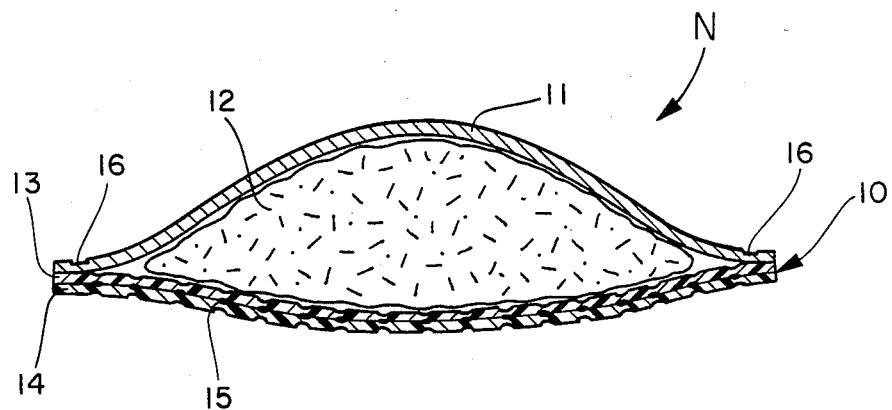

The invention may be more readily understood by reference to the drawings in which:

FIGS. 1 and 2 are end cross sections of different configurations of sanitary napkins having external baffles.

As can be seen in FIG. 1, a sanitary napkin N has an absorbent component 12 completely encircled by a largely moisture impenetrable cover 11. Attached to the bottom overlap portion of the largely moisture impenetrable cover 11 is the baffle 10 of this invention having layers 13 and 14. Layer 13 is a meltblown microfibrous web such as described in the Naval Research Lab Report No. 4364 of May 25, 1964 which is hereby incorporated by reference. This baffle layer facing the absorbent preferably made of polypropylene although other olefinic fibers may be used. It is preferred that this web contain relatively small orifices and this is accomplished by utilizing small diameter fibers generally in the range of 10 microns or below which are closely formed to provide small capillaries. A suitable web with these microfibers has a basis weight between 13.0 and 28.0 grams per square meter. The relatively small capillaries provide for gas and vapor transfer while minimizing but not completely stopping fluid transfer. It has been found that meltblown webs of this type do not have the strength to resist tearing when a garment attachment adhesive is applied directly to it and, therefore, it is totally unsuitable as a baffle material. Also, while a meltblown baffle can be rendered fluid impermeable by densifying the web to a considerable extent, the desirable textural properties are destroyed when this is done.

Attached to the meltblown web 13 is a separate spunbonded web 14. Spunbonded polyolefinic webs are described for example in U.S. Pat. No. 3,692,618 which is hereby incorporated by reference. This spunbonded polyolefinic filament web when maintained at a basis weight of not less than 8 grams per square meter provides sufficient strength for the addition of garment attachment adhesive and the subsequent removal of the napkin from the undergarment without tearing of the baffle. Due to low product weight and fiber filament size, the spunbonded web does not provide a gas or vapor barrier even when joined to the meltblown web.

A way of measuring textural feel of cloth or other webs is a measurement of "hand". Hand is a combination of surface friction and flexural rigidity. A conventional apparatus used for measuring these characteristics are a Thwing-Albert Handle-o-meter. Such a device has an opening over which the material to be measured is placed. A push rod then is lowered at a constant rate of speed and the force necessary to bend the textile sample through the opening is measured. On a Handle-o-meter Model 211-5, having a slot opening of 0.5 inches, a penetrator blade i.e., push rod of 0.125, inches and a product sample size of 4" by 4", the hand measurement is between 12 and 20 grams for a suitable flexible baffle composite. The baffle composite can be formed by permanent adhesive bonds or, more preferably, by fusing as shown by a fusing pattern with individual fuse spots 15 in FIGS. 1 and 2. If the baffle components are to be fused, the spunbonded and the meltblown baffle material must be compatible, i.e., they must melt at approximately the same temperature to provide the joining of the layers. If the webs are fused which, as is well known in the art, can be readily done under suitable conditions of heat and pressure, the bond area between the baffle layers is not less than 5% and is preferably between 10 and 25%. Obviously, no fluid will pass at the particular bond sites.

It may be desirable to add a water repellent coating to the baffle composite. The composite after formation can be readily subjected to a dip process and a suitable water-proof coating for the composite is a 3M fluorocarbon water repellent designated as FC-808. Other suitable fluorocarbons may also be employed and, less preferred, because of the negative textural effects are the silicone water repellent treatments. The baffle composite itself may be attached to the other components of the napkin adhesively or by fusing them to the nonwoven web or the bottom of the absorbent component or to both. In the embodiment depicted at FIG. 2, a nonwoven thermoplastic cover is fused to the composite baffle where the edges of the baffle and cover extend beyond the periphery of the absorbent at either side of the sanitary napkin.

It is apparent that the baffle described herein can also be used for other absorbent products although strength and resistance to tear will not be as great a factor where there is no pressure sensitive garment attachment adhesive employed.

We claim:

1. In a sanitary napkin with a top surface and a bottom surface comprising a fluid pervious cover on a top surface an absorbent positioned beneath said cover and an essentially moisture impermeable baffle forming a bottom surface of said napkin, and pressure sensitive garment attachment adhesive attached to the bottom surface the improvement characterized by said baffle being formed by a multi-layer composite of a spunbonded polymeric web of at least 8 grams per square meter and a meltblown polymeric web between 13.0 and 28.0 grams per square meter with said adhesive attached to said spunbonded web.

2. The napkin according to claim 1 wherein the composite is formed by fusing.

3. The napkin according to claim 2 wherein the fused bond area is at least 5%.

4. The napkin according to claim 2 wherein the fused bond area is between 10 and 30%.

5. The napkin according to claims 1, 2 or 3 wherein the composite has been treated with a fluid repellent compound.

6. The napkin according to claim 2 wherein the polymers are compatible.

* * * * *